United States Patent
Scolaro

(10) Patent No.: US 10,244,936 B2
(45) Date of Patent: Apr. 2, 2019

(54) METHOD AND APPARATUS FOR ENGAGING AND PROVIDING VISION CORRECTION OPTIONS TO PATIENTS FROM A REMOTE LOCATION

(71) Applicant: Johnson & Johnson Vision Care, Inc., Jacksonville, FL (US)

(72) Inventor: James Michael Scolaro, Ponte Vedra Beach, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 242 days.

(21) Appl. No.: 13/944,524

(22) Filed: Jul. 17, 2013

(65) Prior Publication Data

US 2014/0028973 A1    Jan. 30, 2014

Related U.S. Application Data

(60) Provisional application No. 61/675,524, filed on Jul. 25, 2012.

(51) Int. Cl.
*A61B 3/00* (2006.01)
*G02C 7/02* (2006.01)
(Continued)

(52) U.S. Cl.
CPC ............ *A61B 3/0025* (2013.01); *G02C 7/027* (2013.01); *G06F 19/3418* (2013.01);
(Continued)

(58) Field of Classification Search
CPC ......... A61B 3/14; A61B 3/102; A61B 3/0025; A61B 3/113; A61B 3/12; A61B 3/0008;
(Continued)

(56) References Cited

U.S. PATENT DOCUMENTS 6,086,204 A * 7/2000 Magnante ............ A61B 3/1015
219/121.75
2005/0073648 A1    4/2005 Toshima et al.
(Continued)

FOREIGN PATENT DOCUMENTS

CN    1612714 A    5/2005
EP    2228771 A2    9/2010
(Continued)

OTHER PUBLICATIONS

Written Opinion issued by the Intellectual Property Office of Singapore for Application No. 2013056551 dated Oct. 31, 2014.
(Continued)

*Primary Examiner* — Thomas K Pham
*Assistant Examiner* — Sharrief I Broome

(57) ABSTRACT

A method and system for providing vision correction to a patient is disclosed. The method and system employ a vision care POD to engage and provide vision diagnostics and correction options to a patient. More specifically, method and system may include educating the population of a geographic area through sources that target particular identified groups in need of vision correction; providing an eye examination to patients using a vision care POD to generate a personalized vision correction ID card; providing one or more vision correction solution(s) to the patient; supplying the patient with the one or more vision correction solution(s) and the corresponding training for the solution(s); and providing ongoing care and support to the patient.

1 Claim, 4 Drawing Sheets

(51) Int. Cl.
    *G06F 19/00*     (2018.01)
    *G16H 10/65*     (2018.01)
    *G16H 50/50*     (2018.01)

(52) U.S. Cl.
    CPC ........ *F04C 2270/041* (2013.01); *G16H 10/65* (2018.01); *G16H 50/50* (2018.01)

(58) Field of Classification Search
    CPC ........... A61B 3/10; A61B 3/032; A61B 3/107; A61B 3/1025; A61B 3/103; A61B 3/1005; A61B 3/1015; A61B 3/18; A61B 3/117
    USPC .................................................. 351/200–246
    See application file for complete search history.

(56) References Cited

U.S. PATENT DOCUMENTS

| | | | |
|---|---|---|---|
| 2005/0105048 A1* | 5/2005 | Warden | B24B 13/00 351/159.01 |
| 2006/0152675 A1 | 7/2006 | Toshima et al. | |
| 2006/0189966 A1* | 8/2006 | Lieberman | A61B 3/107 606/12 |
| 2007/0097318 A1* | 5/2007 | Chehab | A61B 3/103 351/211 |
| 2008/0198328 A1 | 8/2008 | Seriani | |
| 2009/0053351 A1* | 2/2009 | Widman | B29D 11/00134 425/174.4 |
| 2010/0030570 A1 | 2/2010 | Kratzer | |
| 2010/0033678 A1* | 2/2010 | Foster | 351/223 |
| 2010/0296055 A1* | 11/2010 | Esser | A61B 3/0025 351/204 |
| 2011/0027766 A1 | 2/2011 | Yoo | |

FOREIGN PATENT DOCUMENTS

| | | |
|---|---|---|
| JP | 2001305495 A | 10/2001 |
| JP | 2004513389 A | 4/2004 |
| JP | 2004527777 A | 9/2004 |
| JP | 2008059548 A | 3/2008 |
| JP | 2008508006 A | 3/2008 |
| JP | 2008512142X | 9/2009 |
| WO | WO2006010611 A1 | 2/2006 |

OTHER PUBLICATIONS

EP Search report for corresponding EPA No. 13178061.1 dated Jul. 31, 2017.

Search reports for corresponding TW Appln. No. 102126393 dated Jul. 31, 2017 Apr. 26, 2017 & Oct. 16, 2017.

* cited by examiner

METHOD AND APPARATUS FOR ENGAGING AND PROVIDING VISION CORRECTION OPTIONS TO PATIENTS FROM A REMOTE LOCATION

CROSS-REFERENCE TO RELATED APPLICATION

This application claims the benefit of U.S. Provisional Application No. 61/675,524, filed Jul. 25, 2012.

BACKGROUND OF THE INVENTION

1. Field of the Invention

The present invention relates to vision correction, and more particularly to methods and apparatus for engaging and providing personalized vision correction options, instructional information, and ongoing support to patients. More specifically, the methods and systems of the present invention employ a remote vision care POD used to examine a patient's vision.

2. Discussion of the Related Art

A large portion of the population is ametropic; i.e., their vision is less than optimum due at least in part to refractive abnormalities of the eye. For over one-hundred (100) years, practitioners ranging from lens fitters to surgeons have engaged in the business of providing vision correction to the ametropic population, as technology permitted, through spectacles, contact lenses, intra-ocular lenses (IOLs), corneal inlays and corneal onlays.

Many visual defects, also commonly known as aberrations, may arise from refractive abnormalities that have an adverse impact on the imaging properties of an eye. Multiple orders of aberrations that may affect vision may be described using a variety of mathematical models, an example of which are Zernike coefficients. A set of Zernike coefficients thus gives detailed information on the relative and absolute importance of the different aberrational defects of any particular eye for the specified conditions of measurement. In the Zernike description, first-order polynomials describe wavefront tilt (i.e., prismatic effects) and have no effect on image quality. Second-order polynomials describe the sphero-cylindrical errors of focus which can normally be negated by optical corrections, such as spectacles or contact lenses.

While spectacles, contact lenses, and the like generally provide optical correction to help people see better, there is a need in some geographical areas of the world for the engagement of the population through facilitated testing for vision correction and eye care education, and ongoing support to those individuals. Accordingly, there is a need for new methods and systems that can facilitate proper testing and ongoing support to individuals situated in those geographical areas. Such methods and systems should be simple to understand and use, yet provide for patient preferences and/or needs matching.

SUMMARY OF THE INVENTION

The methods and systems in accordance with the present invention overcome the disadvantages and concerns as briefly set forth above.

In accordance with some aspects of the present invention, exemplary method steps that may be implemented for engaging an identified population and providing vision correction to a patient are provided. The method may include educating the population of a geographic area through sources that target particular identified groups in need of vision correction; providing an eye examination to patients using a vision care POD to generate a personalized vision correction ID card; providing one or more vision correction solution(s) to the patient; supplying the patient with the one or more vision correction solution(s) and the corresponding training for the solution(s); and providing ongoing care and support to the patient.

In accordance with other aspects of the present invention, a method for determining whether a patient needs vision correction is disclosed. The method which implements a vision care POD that may be equipped with automated eye examination devices and in communication with a network in communication with an eye care practitioner to properly identify whether vision correction is needed. If it is determined that vision correction is needed, the vision care POD may generate a personal vision care ID card comprising data including a generated prescription for the patient. Other data may include a patient's preferences, retailer information, appointment data, health history, and lifestyle. The vision care POD may also be in communication with retailers, manufacturer, customer service plant, school, and the like, through the communication network.

It will be appreciated by those skilled in the art that any data transmission referred to above could be in the form of telecom or datacom, and could be sent via wire-based (optical fiber, cable, etc.) or wireless services. A preferable interface would be Internet based.

In some exemplary embodiments of the present invention, the vision care POD may additionally generate and display a simulation comparing what the patient would see with the selected vision correction contact lenses or spectacles. Similarly, the vision care POD may generate and display what the patient would look like with the selected vision correction contact lenses and spectacles. Further, a patient's preferences may be obtained and included in the generated personalized vision care ID card that may be used in various associated entities.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PRESENT EMBODIMENT

Figure 1:
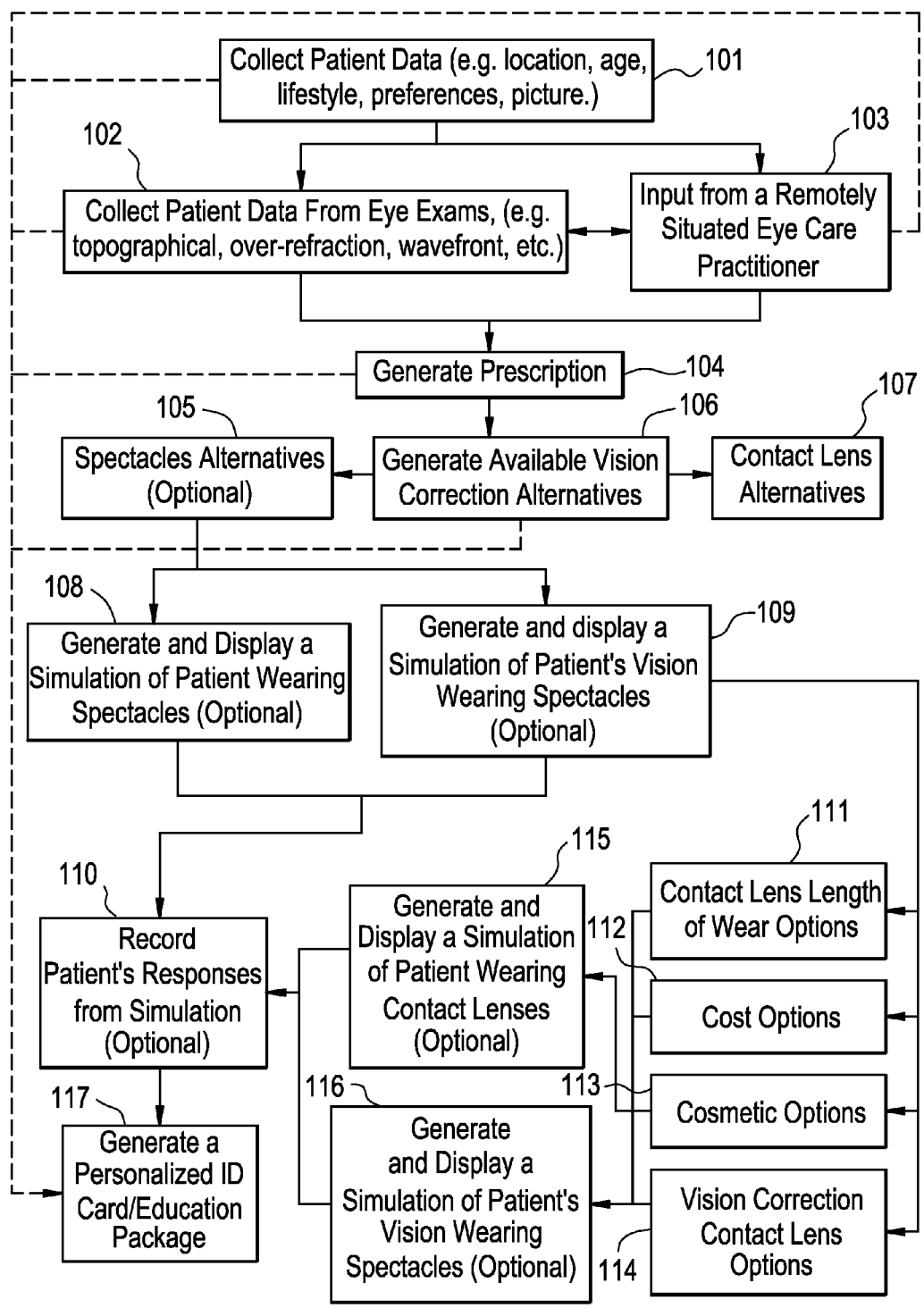
FIG. 1 is a flowchart illustrating exemplary method steps that may be implemented for providing a personalized vision care ID card to a patient in accordance with the present invention.

The present invention relates to methods and systems useful to engage patients and provide vision correction options to them. In the following sections, detailed descriptions of exemplary embodiments of the present invention will be given. The description of both preferred and alternate embodiments are exemplary embodiments only, and it is understood that to those skilled in the art that variations, modifications and alterations may be apparent. It is therefore to be understood that the exemplary embodiments do not limit the scope of the underlying invention.

Glossary

In this description and claims directed to the present invention, various terms may be used for which the following definitions will apply:

"Custom Product" as used herein, refers to a product including one or more parameters that may be available in other than customary or standard products and/or settings. Custom product parameters may allow for more precisely targeted sphere power, cylinder power, and cylinder axis (e.g., −3.125D/−0.47D×18°) than standard products. The customized settings may also relate to base curves, diameters, stabilization profiles, and thickness profiles based upon a particular product offering and the intended use of the product. A custom product may be formed using a free form technique, such as, one described in U.S. patent application Ser. No. 12/194,981 filed on Aug. 20, 2008 and in U.S. patent application Ser. No. 12/195,132 filed on Aug. 20, 2008 both of which are incorporated by reference herein.

"Eye Care Practitioner" as used herein refers appropriately to anyone qualified to fit, prescribe or dispense vision correction devices such as spectacles, contact lenses and the like, or medically attend to a patient particularly with respect to the patient's eyes.

"Eye Data" as used herein, means the data and information taken of a patient's eye when the patient is not using any vision correction devices. A series of exams may be performed to collect bare eye data, including, e.g., a physiology exam, a topographical exam, a wavefront exam, and a refraction exam.

"Lens" as used herein, refers to any ophthalmic device that resides in or on the eye. These devices may provide optical correction or may be cosmetic. For example, the term lens may refer to a contact lens, intraocular lens, overlay lens, ocular insert, optical insert or other similar device through which vision is corrected or modified, or through which eye physiology is cosmetically enhanced (e.g., iris color) without impeding vision. In some exemplary embodiments, the preferred lenses of the invention are soft contact lenses and are made from silicone elastomers or hydrogels, which include but are not limited to silicone hydrogels, and fluorohydrogels.

"Physiology Exam" as used herein means an exam that observes the physical appearance of the eye. Physiology exam includes, but is not limited to, a glaucoma test (e.g., tonometry test, ophthalmoscopy, optic nerve computer imaging techniques, etc.), a retinal exam (e.g., ophthalmoscopy, papillary dilation test, optomap retinal exam, etc.), checking for ulcers, a tear production test to check for dry eye syndrome (e.g., Schirmer test), checking for eye infections, and the like.

"Refraction Exam" as used herein means an exam wherein a patient's vision is refracted using a device that contains hundreds of combinations of lenses to determine any possible refractive error such as nearsightedness, farsightedness, astigmatism, or presbyopia. An over-refraction exam is where a similar exam is taken but with the patient wearing a contact lens.

"Standard Product" as used herein, refers to a product with limited product parameter availability, such as those currently offered with specified settings that vary in discrete steps. For example, standard products could define a family of products where sphere power parameters may only be available in 0.25D steps (e.g., −3.00D, 3.25D, −3.50D, etc.); cylinder power parameters may only be available in 0.50D steps (e.g., −0.75D, −1.25D, −1.75D, etc.); and cylinder axis parameters may only be available in 10° steps (e.g., 10°, 20°, 30°, etc.). Other standard product parameters and features offered in discrete steps include but are not limited to base curve radii, diameter, stabilization profiles and thickness profiles.

"Store-Based" as used herein means an interaction between the patient and information utilizing devices or information source elements occurring at various points (e.g., practitioner's office, pharmacy, retail store, on-line, POD/Kiosk, mobile center, and the like).

"Topographical Exam" as used herein means an exam that looks at the surface features of an eye. A topographical exam includes, but is not limited to, curvature of a cornea and surface of a retina, which may help in determining certain characteristics such as: base curve measurement of a patient's eye, limbal measurements, pupil size, line of sight measurement, pupil center measurement, geometric center measurement, and the like.

"Vision Correction" as used in the description of the invention refers both to a measured improvement in vision over that provided by conventional refractive correction and to the subjective evaluation of "seeing better" by the patient.

"Wavefront Exam" as used herein means an exam that looks at the way that the light travels in an eye. A wavefront exam, which may be performed with an aberrometer, creates an optical aberration map, which is sometimes called an "optical fingerprint," and identifies optical aberrations or distortions of a patient's eye (e.g., low order, medium order, high order, Zernike, other functions or descriptors, and the like). Examples of low order optical aberrations include nearsightedness, farsightedness, and astigmatism. Examples of high order optical aberrations include coma, trefoil, and spherical aberration.

"Web-Based" as used herein means an interaction between a practitioner and/or a patient and information based on communication, either in near real time or by delayed transmission, between two points, in which this connection uses in part the Internet, commonly referred to as the World-Wide-Web, where a practitioner and/or a patient is at one of the points. The practitioner and/or the patient located point can be a store or non-store location (i.e., home, POD/Kiosk, or office) for such a web-based interaction.

Certain information regarding a patient may be used to assist in the selection of vision correction products. The method of the present invention centers on the ability to engage populations of particular geographical areas to properly identify the needs and preferences of patients and to match these needs and preferences with appropriate vision correction products.

Referring now to FIG. 1, there is illustrated a flowchart showing exemplary method steps that may be implemented for providing a personalized vision care ID card to a patient. At step 101, patient data may be collected, for example, through the use of questionnaires. Questionnaire content may include questions such as age, gender, geographic location, lifestyle, preferences, personal history, symptoms, practitioner information, vision correction needs, contact lens interest, free trial interest, and any other information which may be useful for constructing or maintaining one or more databases for future use. Each question may be associated with one or more input devices such as radio button, drop-down menu, or check-box for example, such that upon submission by the user, the data is stored by the client engine and/or server such as by entry into a database such that the data is available for access at a later time. The information may be stored temporarily or permanently in various exemplary embodiments and may be employed when recommending different product choices for the patient. Preferably the information may be stored in a generated personalized vision care ID, held by the patient, for uses described in other parts of this disclosure.

At step 102, patient eye data may be collected within a vision care POD/Kiosk equipped with equipment used to obtain certain ocular measurements and characteristics. This may include one or more automated or conventional systems/devices for performing a physiology exam, refraction exam, topographical exam, and wavefront exam. In preferred exemplary embodiments, the different examinations may be fully automated processes requiring very minimal end-user involvement. At step 103, a remotely located eye care practitioner may access the collected data and using telemedicine techniques may communicate with the patient explaining the results of his/her analysis of the data. The eye care practitioner may discuss whether a vision correction treatment is needed and provide an explanation of the treatment, for example, spectacles and contact lenses. Further, if the doctor sees anything that would suggest a further, more detailed examination is needed, the patient may be directed to a hospital or specialist for a more comprehensive examination.

At step 104, a prescription may be generated. The prescription may be generated from the data gathered alone or additionally with input from the eye care practitioner. Based on the prescription correction, alternatives may be presented to the patient, step 106. For example, different types of contact lenses, step 107, or spectacles 105 may be selected. During the selection of spectacles, a software generated simulation of the patient's vision wearing the spectacles compared to without the spectacles may be displayed to the patient, step 109. Furthermore, using a picture or still frame of video collected, a software generated simulation of what the patient would look like wearing the spectacles may be displayed to the patient, step 109.

At step 107, contact lens alternatives may be presented to the patient based on vision correction needs. However, the patient may select different preferences, such as length of wear options, step 111 (e.g. one day disposable, weekly, and the like), cost options, step 112, cosmetic options, step 113 (e.g. color enhancer lenses, color changing lenses, lenses with a color lumbar ring, and the like) lens options, step 114 (e.g. comfort, requirements, and the like). Similarly, software generated simulations of vision correction, step 115 and/or what the user may look like wearing the selected contact lenses, step 116, including both custom products and standard products, may be displayed to the patient. Furthermore, a comparison of the patient wearing spectacles simulation representation may be displayed next to a simulation representation of the patient wearing contact lenses may be displayed to the patient. It may be possible to include a software tool that includes manipulator tools, such as the one described in U.S. patent application Ser. No. 12/401,662, titled "INTERACTIVE CONTACT LENS SIMULATION SYSTEM AND METHOD" of the same inventive entity to be included in the vision care POD. The contents of the application referenced which are incorporated by reference and relied upon. From the simulations and user preferences, the patient may select various options which may also be recorded as additional preferences, step 110, for example, from the responses to the different simulations displayed.

At step 117, data may be classified and stored in a personalized vision care ID card. It is also possible for some or all of the information regarding the selection of vision correction options, in accordance with the methods of the present invention, to be distributed to eye care practitioners, merchants, manufacturer, or other persons and/or places likely to be engaged in the recommendation, retail sale, promotion, distribution, giveaway, or trade of eye care products taking into account privacy rights of the patients.

Figure 2:
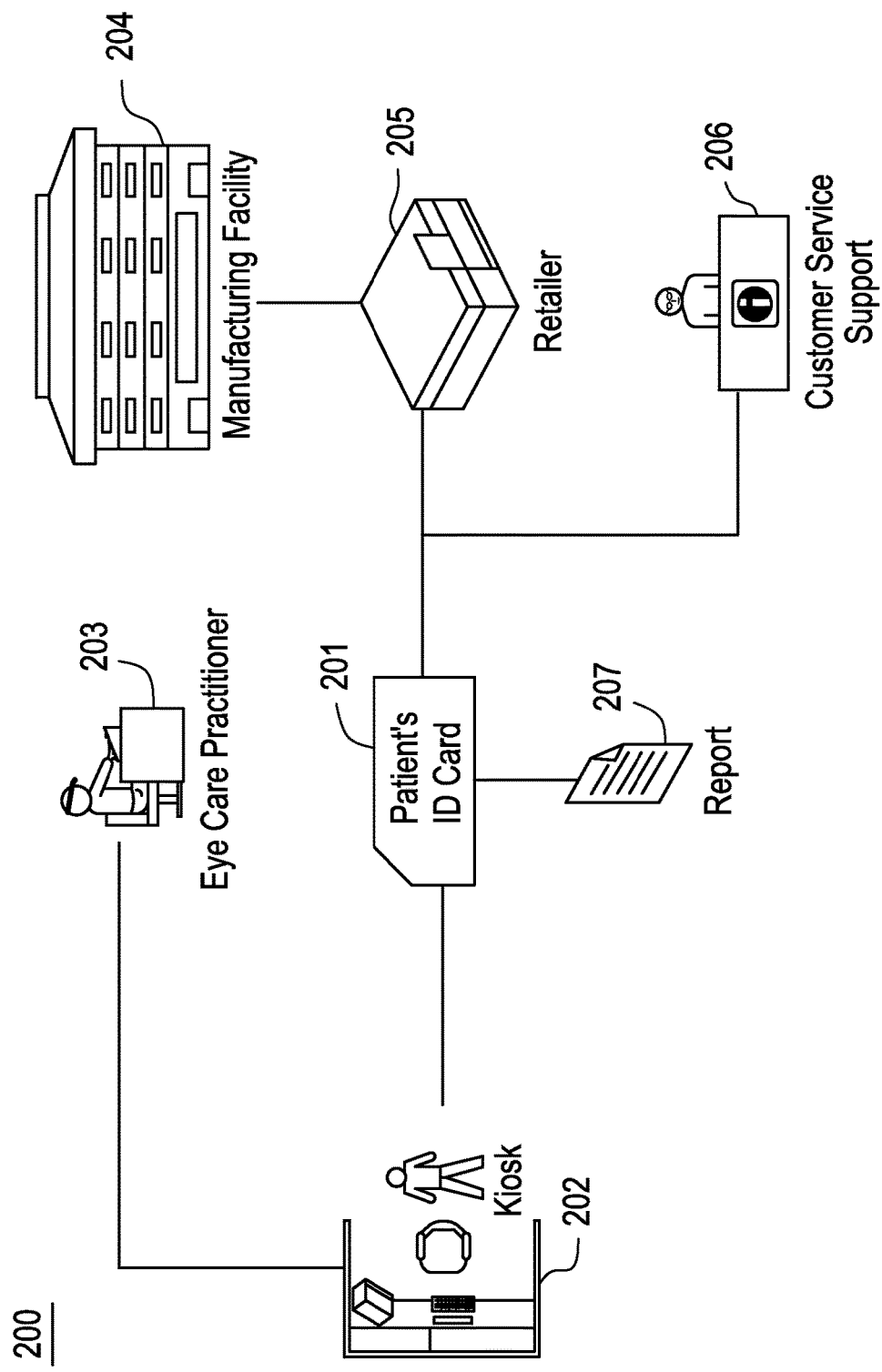
FIG. 2 illustrates a network for the transfer of information between entities that may be implemented in accordance with the present invention.

Referring now to FIG. 2, exemplary entities that form part of a network that may be implemented in accordance with some aspects of the present invention for the transfer of information between them are depicted. The information may be transmitted via the internet; however, any supporting transmission mode and transmission medium may be used. For example, the information may be transmitted by computer, mail, wireless device, telephone, or any other modes imaginable that may be used for data transmission. In the exemplary representation, a patient may engage himself/herself in a vision care POD or kiosk 202. The vision care POD 202 may be located, for example, at a school or near any point of interest. A remotely located eye care practitioner may be in communication with the vision care POD 202 using any one method known to provide medical telemedicine to the patient as described in other parts of this disclosure. The information may be stored in or on a personalized vision care ID card 201 which may be updated as desired or required and used to generate a report 207 for the patient and/or directly implemented by a manufacturing facility 204 (e.g. to complete and order), a retailer 205 (e.g. to verify a prescription), and/or by customer service support 206 (e.g. to verify information of the patient and product ordered).

Figure 3:
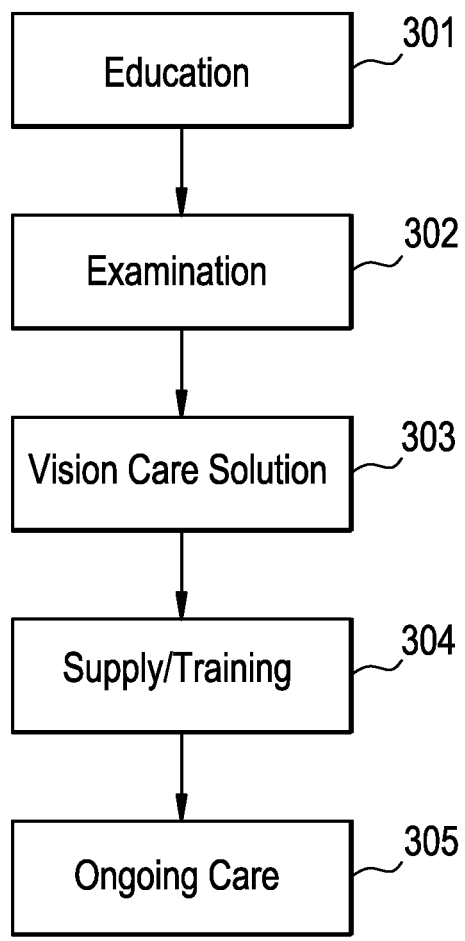
FIG. 3 is a flow chart illustrating exemplary method steps that may be implemented to engage and provide continuous vision care to patients in accordance with the present invention.

Referring now to FIG. 3, a flow chart showing exemplary method steps that may be implemented to engage and provide continuous vision care to patients is depicted. At step 301, the population of a particular geographical area may be provided with vision care education. An educational package may include the generated personalized vision care report and suggested products, as well as generic packages for students, athletes, parents, and the like. The package may be represented through any suitable means including paper media, digital media, and seminars/functions.

At step 302, examination may take place through the use of a vision care POD to generate a personalized vision care ID card/report, as described with respect to other parts of the present invention. Additionally, the vision care POD may include a user interphase, such as a touch screen, mouse, voice recognition, and the like to input responses and in some embodiments to generate a user name and password for information to be send electronically through e-mail to the patient, parent, or associated entity.

When vision correction need is identified, the patient may also be sent information regarding the diagnosis and directed to schedule an appointment to see a vision care specialist, for example, an ophthalmologist, using the vision care POD. This appointment may be a web-based scheduling tool coordinated through the a variety of entities with eye care practitioners. During a scheduled vision care appointment occurring at a vision care POD, the following steps may take place. The patient may enter either their ID card or personal vision care ID number and password into the POD. With that information entered, all of the personal vision care profile information along with the results of the preliminary exam relating to that individual is readily available. In addition, the patient may be directed to go through a series of steps in which the machine may collect one or more of a prescription of current glasses if available, a pupil distance measurement, a close up picture of each eye (16-18 mm wide field of view) with all parts of eye in focus, a full face photograph of the patient, a measure from the corner of the eye to the back of the ear and middle of the ear hole, and an additional vision test.

At step 303, a vision correction solution may be provided to the patient. The solution may be provided by the prescription alone, but preferably the patient may request or be offered the virtual reality phase of the appointment described at steps 108, 109, 115 and 116 (FIG. 1). This step may take place in the vision care POD and enable the patient to experience how vision care solutions will impact their vision. The complete information may be stored under the personalized vision care profile and ID card. The patient may additionally receive a personalized report explaining all of their data and vision care options and directed to a retail outlet.

At step 304, the patient may be supplied the product and provided training on the use of the particular product. For example, a patient may go to a retailer. This retailer may be set up to supply patients with all of the products, information, and training under the vision care POD program. The process at the retailer may include utilizing the data from the personalized ID card and providing the patient with the pre-selected spectacles/contact lenses. The retailer may conduct the proper fitting and training on care of the spectacles/contact lenses. When contact lenses are desired, a patient may be trained on insertion, removal, care, and use of the contact lenses. Information may be gathered from the purchase and sent to the different entities through the communication network for different purposes, such as tracking of the lenses or statistical analysis.

At step 305, the patient may be provided with ongoing care and support. For example, it may include follow-up for bi-annual or yearly exams, answering any questions regarding the products, discounted offers or additional product releases, loyalty points, and the like.

Figure 4:
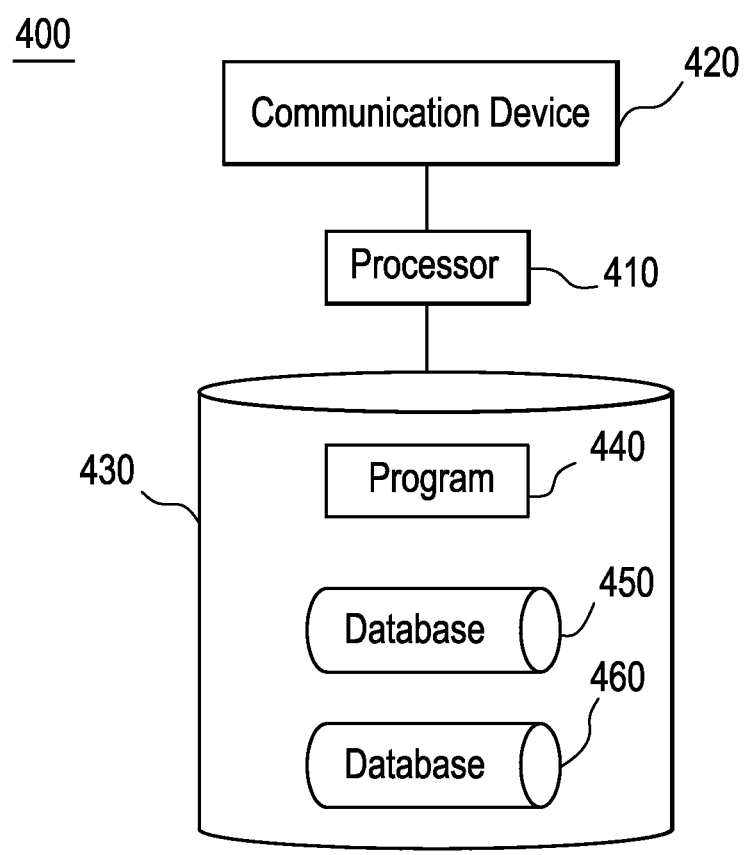
FIG. 4 illustrates a schematic diagram of an exemplary processor that may be utilized in accordance with the present invention.

Referring now to FIG. 4, there is illustrated a schematic diagram of an exemplary controller 400 processor that may be utilized in accordance with the present invention. The exemplary controller 400 includes a processor 410, a communication device 420 and a data storage or memory component 430. The processor 410 is in communication with both the communication device 420 and the data storage device 430. The communication device 420 may be configured to communicate information via a communication channel, wired or wireless, to electronically transmit and receive digital data related to the functions discussed herein. The communication device 420 may also be used to communicate, for example, with one or more human readable display devices, such as, an LCD panel, an LED display or other display device or printer. The storage device 430 may comprise any appropriate information storage device, including combinations of magnetic storage devices (e.g., magnetic tape, radio frequency tags, and hard disk drives), optical storage devices, and/or semiconductor memory devices such as Random Access Memory (RAM) devices and Read-Only Memory (ROM) devices. The storage device 430 may store the modeling program 440 for controlling the processor 410. The processor 410 performs instructions of the program 440, and thereby operates in accordance with the present invention. For example, the processor 410 may receive information relating to patient collected data, profiles, measured data, and the like. The storage device 430 may also store and send all or some of the information sent to the processor 410 in one or more databases 450 and 460.

A number of exemplary embodiments of the present invention have been described herein. While this specification includes specific implementation details, they should not be construed as limitations on the scope of any inventions or of what may be claimed, but rather as descriptions of features specific to particular embodiments of the present invention.

Certain features that are described in this specification in the context of separate embodiments may also be implemented in combination in a single embodiment. Conversely, various features that are described in the context of a single embodiment may also be implemented in combination in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous. Nevertheless, it will be understood that various modifications may be made without departing from the spirit and scope of the claimed invention.

What is claimed is:

1. A patient POD for engaging and providing vision correction support, the patient POD comprising a processor having an input means for collecting patient data; equipment to obtain various ocular measurements and characteristics, including data from a physiology examination, a refractive examination, a topographical examination and a wavefront examination; a transmission medium for providing two-way communication between a patient and an eye care professional to determine options for treatment if required; a display for providing simulations of both the impact of vision correction and how the patient would look with the vision correction means; a device for storing data and generating a patient ID card with the data thereon, and an apparatus for forming a custom lens that resides on or in the eye directly from the ocular measurements and characteristics, the custom lens including targeted sphere power, targeted cylindrical power and axis, targeted diameter, targeted stabilization profiles and targeted thickness profiles, the apparatus being configured to form the custom lens from a lens precursor that resides on or in the eye utilizing a free form technique wherein the surfaces of the custom lens are formed by cross-linking of a reactive mixture, the apparatus comprising a first apparatus for forming a lens precursor, the first apparatus comprising a substrate including an arcuate surface, wherein at least a portion of the substrate includes an optical quality surface and a source of actinic radiation controllable to cure a portion of the reactive mixture from the optical quality surface in a predetermined pattern on a voxel by voxel basis, and a second apparatus for forming a lens based upon the lens precursor, the second apparatus comprising a light source for emitting actinic radiation, a means for focusing the actinic radiation, a mold part comprising a lens forming surface transmissive of sufficient converging light from the means for focusing to comprise actinic radiation, a vessel for containing reactive mixture around the lens forming surface in an amount in excess of an amount required to form the lens precursor, a material removal device operational to remove fluent reactive mixture, a dwelling location where the mold part can be positioned such that flowable chemical residue may flow across the near surface region of the lens precursor and a source of fixing radiation sufficient to fix unreacted and partially reacted monomer forming the lens precursor to form the lens based upon the lens precursor.

* * * * *